United States Patent

Falchetto

[11] Patent Number: 6,121,484
[45] Date of Patent: Sep. 19, 2000

[54] METHOD FOR PRODUCING ARYLCYANATES

[75] Inventor: Alessandro Falchetto, Montecrestese, Italy

[73] Assignee: Lonza AG, Gampel/Valais, Switzerland

[21] Appl. No.: 09/308,565

[22] PCT Filed: Nov. 25, 1997

[86] PCT No.: PCT/EP97/06579

§ 371 Date: May 21, 1999

§ 102(e) Date: May 21, 1999

[87] PCT Pub. No.: WO98/23584

PCT Pub. Date: Jun. 4, 1998

[30] Foreign Application Priority Data

Nov. 29, 1996 [CH] Switzerland .............................. 2936/96

[51] Int. Cl.[7] .................................................. C07C 261/00
[52] U.S. Cl. .......................................................... 560/301
[58] Field of Search ............................................... 560/301

[56] References Cited

U.S. PATENT DOCUMENTS 4,022,755  5/1977  Tanigaichi et al. .

FOREIGN PATENT DOCUMENTS 17 20 663    9/1975   Germany .
25 33 322    2/1976   Germany .
195 19 102
     A1      11/1995  Germany .

*Primary Examiner*—Paul J. Killos
*Attorney, Agent, or Firm*—Fisher, Christen & Sabol

[57] ABSTRACT

Arylcyanates are produced by reacting polyvalent phenols with a halogen cyanogen in the presence of a tertiary amine and a nonaqueous solution at high temperature. The tertiary ammonium halogenide obtained as a secondary product is fully or partially removed by processing the reaction mixture with cationic and anionic exchanger, whereby arylcyanates with a particularly low halogenide content are obtained.

10 Claims, No Drawings

METHOD FOR PRODUCING ARYLCYANATES

BACKGROUND OF THE INVENTION

1. Field of the Invention

The present invention relates to a process for the preparation of aryl cyanates by reaction of polyhydric phenols with cyanogen chloride or bromide in the presence of tertiary amines.

The cyanic esters of polyhydric phenols, referred to in short as aryl cyanates here and below, are starting materials for the preparation of high-temperature-resistant thermosets with a triazine structure (see, for example, DE-A 17 20 663). Here and below, polyhydric phenols are taken to mean, in particular, those compounds in which two or more benzene rings, each of which is substituted by a hydroxyl group, are bonded together via direct bonds, lower di- or polyvalent acyclic hydrocarbon radicals, di- or polyvalent mono- or polycyclic aromatic or cycloaliphatic radicals, heteroatoms, or complex groups composed of the aforementioned radicals. Examples include the various compounds known as bis- and triphenols, such as bisphenol A, and the oligomeric condensation products of formaldehyde and phenols or cresols known under the name novolaks.

2. Background Art

The aryl cyanates mentioned are usually prepared by reacting the corresponding polyhydric phenol or its adduct or salt with a tertiary amine, for example triethylamine, in a nonaqueous solvent such as, for example, acetone, with a cyanogen halide, in particular cyanogen chloride or bromide, at a very low temperature (see, for example, DE-A 195 19 102). The hydrogen halide which forms is bound by the tertiary amine which is present in the phenol-amine adduct or, when a free phenol is used, has been added as such. This produces molar amounts of a tertiary ammonium halide, all of which must be removed, particularly when the prepared aryl cyanate cannot be purified by crystallization or distillation. It is usually removed by extraction with water, optionally with prior filtration or centrifugation of precipitated ammonium halide. However, the only solvents which are highly suitable for this purpose are those which are immiscible with water. The reason for this is that if water-miscible solvents such as, for example, acetone are used, aqueous solvent mixtures are produced which can only be worked up again with great difficulty and must therefore in most cases be disposed of as waste material. However, even when water-immiscible solvents are used, problems frequently arise during phase separation as a result of traces of solvent which remain in the water of extraction and as a result of traces of water in the organic phase, which can make additional drying necessary.

BROAD DESCRIPTION OF THE INVENTION

The object of the present invention was therefore to provide a process with an alternative work-up method which permits simple and complete removal of the ammonium halide produced even when water-miscible solvents are used for carrying out the reaction, without problematic waste materials being produced.

According to the invention, this object is achieved by the process according to patent claim 1.

It has been found that by simply treating the reaction mixture, which is obtained in a manner known per se, with cation and anion exchangers, virtually all of the ammonium halide can be removed. Either the entire amount of ammonium halide or the remainder which is left following partial removal by another method can be removed by means of the ion exchanger treatment. Preferably, most of the ammonium halide is separated off prior to the ion exchanger treatment using a solvent in which the ammonium halide is not readily soluble, and filtering or centrifuging the reaction mixture when the reaction is complete.

The novel process is preferably carried out by treating the optionally filtered or centrifuged reaction mixture firstly with a strongly acidic cation exchanger and then with a weakly basic anion exchanger. It is, however, possible within the scope of the invention to choose another procedure, for example to use a mixed bed of cation and anion exchangers. Examples of suitable cation exchangers are strongly acidic ion exchangers such as Lewatit® S 100 (manufacturer: Bayer AG), and examples of anion exchangers are weakly basic ion exchangers such as Lewatit® MP 62. (If strongly basic ion exchangers are used there is the risk of hydrolysis of the cyanate groups if the contact time is prolonged.) It is essential that the polymeric base materials of the ion exchanger do not dissolve or swell excessively in the solvents used in the novel process. The ion exchanger treatment is advantageously carried out by percolating the optionally filtered or centrifuged reaction mixture in each case through a column packing of the ion exchanger; it is, however, also possible to suspend the ion exchanger(s) in the reaction mixture or filtrate/centrifugate and to remove it/them by filtration or centrifugation when exchange is complete.

The novel process is preferably carried out in a solvent from the group consisting of dichloromethane, di-$C_{1-4}$-alkyl ketones, $C_{1-4}$-alkyl $C_{2-4}$-alkanoates, tetrahydrofuran and acetonitrile or a mixture of these solvents. Here, di-$C_{1-4}$-alkyl ketones are taken to mean ketones with two identical or different linear or branched $C_{1-4}$-alkyl groups, such as, for example, acetone (dimethyl ketone), butanone (methyl ethyl ketone) or diisopropyl ketone. $C_{1-4}$-Alkyl $C_{2-4}$-alkanoates are taken to mean esters of acetic, propionic or (iso)butyric acid with $C_{1-4}$-alcohols.

Particularly preferred solvents are dichloromethane, acetone and butyl acetate.

Further work-up following the ion exchanger treatment can be carried out in a manner known per se. Advantageously, most of the solvent is firstly distilled off. This can subsequently be worked up, for example by rectification, and returned to the process. Crystallizable aryl cyanates such as, for example, bisphenol A dicyanate, can be crystallized directly from the concentrated solution produced in the still of the solvent distillation or be isolated as melts. Noncrystallizable aryl cyanates such as, for example, novolak cyanates are expediently subjected to vacuum distillation, for example in a falling-film evaporator, in order to remove volatile impurities such as dialkylcyanamides and solvent residues. After their exchange capacity has been exhausted, the ion exchangers loaded with the tertiary ammonium ions and the halide ions can be regenerated again in a customary manner using a strong acid (cation exchanger) or a moderately strong to strong base (anion exchanger) and be reused.

The reaction of the polyhydric phenols with the cyanogen halide can be carried out either batchwise, for example in a stirred reactor, or continuously. A continuous procedure is described, for example, in DE-A 195 19 102.

The arylcyanates which can be prepared according to the invention can, for example, be described by the general formula

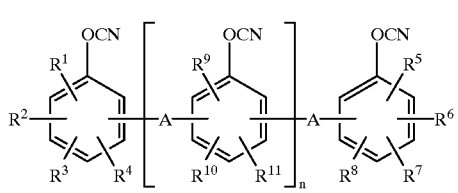

in which n is an integer from 0 to 20, preferably from 0 to 10. Thus, both bifunctional and polyfunctional (oligomeric) aryl cyanates are covered by formula I. The latter are derived, for example, from polyhydric phenols of the novolak type.

A can either be a direct chemical bond or a divalent group. Possible divalent groups are, for example, —O—, —S(O)$_x$— where x=0 to 2, —C(O)—, —OC(O)O—, linear or branched, optionally fluorine-substituted $C_{1-10}$-alkanediyl groups, divalent mono- or polycyclic aromatic radicals which can optionally be substituted with one or more $C_{1-4}$-alkyl groups and/or one or more halogen atoms, divalent mono- or polycyclic cycloaliphatic radicals, which can optionally be substituted with one or more $C_{1-4}$-alkyl groups, and the divalent groups composed of two or more of the aforementioned divalent groups. If n is greater than zero and thus two or more divalent groups A are present, these can be identical or different. Preferably, the groups A are identical.

The substituents $R^1$ to $R^{11}$ can be identical or different and, as well as hydrogen, can each be halogen, $C_{1-4}$-alkoxy, $C_{1-4}$-alkylthio, $C_{1-4}$-alkoxycarbonyl or $C_{1-4}$-alkyl which can be optionally completely or partially substituted by fluorine.

The divalent groups A and also the substituents $R^1$ to $R^{11}$ can each be in the ortho-, meta- or para-position relative to the cyanate groups, it being possible for the substitution pattern on the individual aromatic rings both within one molecule and from molecule to molecule to be different.

The term "alkanediyl group" is here and below taken to mean either those groups whose free valences originate from the same carbon atom, such as, for example, methylene, ethylene or 1-methylethylidene (="iopropylidene"), or those whose free valences originate from different carbon atoms, such as, for example, 1,2-ethanediyl (="ethylene") or 1,3-propanediyl (="trimethylene").

An example of a fluorine-substituted alkanediyl group is 1-(trifluoromethyl)-2,2,2-trifluoroethylidene.

The term "polycyclic" is here and below taken to mean all cyclic structures which have at least two rings. These include singly bonded rings such as, for example, biphenyl, spiro compounds, condensed ring systems such as, for example, naphthalene, bridged ring systems such as, for example, norbornane, and systems which have two or more of these features, such as, for example, octahydro-4,7-methanoindene.

Divalent aromatic radicals are, for example, o-, m- and p-phenylene and the various isomeric napthalenes and biphenylenes.

In the case of the divalent cycloalphatic radicals, the two free valences can originate from the same carbon atom, such as, for example, in the case of cyclohexylidene, or from different carbon atoms, such as, for example, in the case of octahydro-4,7-methanoindenediyl.

Composite divalent groups are, for example, those of the formulae

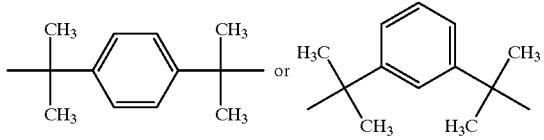

In particular, the novel process is suitable for preparing the following aryl cyanates:

4,4'-Thiodiphenyl cyanate of the formula

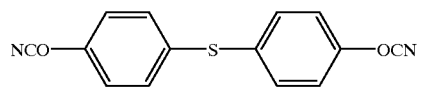

4,4'-Methylenebis(2,6-dimethylphenyl cyanate) of the formula

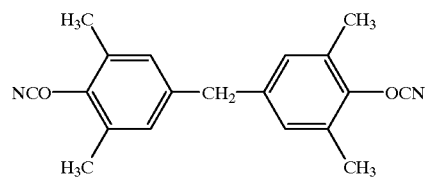

Aryl cyanates of the formula

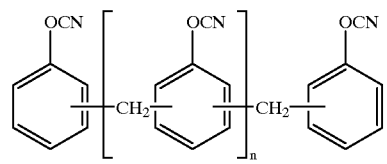

4,4'-Ethylidenediphenyl cyanate of the formula

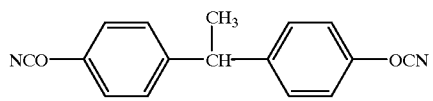

2,2-Bis(4-cyanatophenyl)propane of the formula

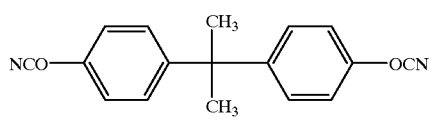

4,4'-[Bis(trifluoromethyl)methylene]diphenyl cyanate of the formula

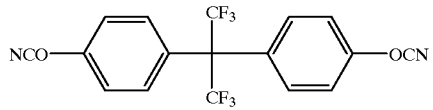

Aryl cyanates of the formula

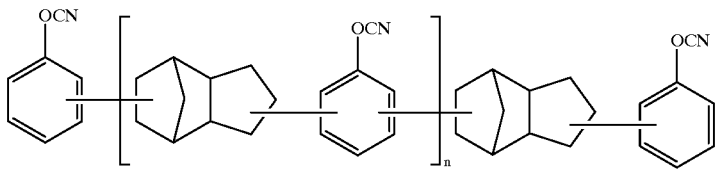

4,4'-(1,3-Phenylenediisopropylidene)diphenyl cyanate of the formula

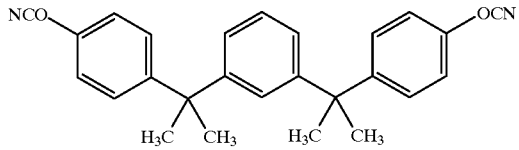

4,4'-(1,4-Phenylenediisopropylidene)diphenyl cyanate of the formula

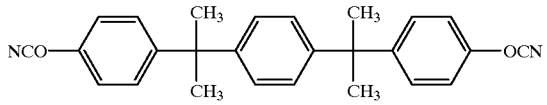

DETAILED DESCRIPTION OF THE INVENTION

The examples below illustrate how the novel process is carried out, but are not intended to impose any limitations.

EXAMPLE 1

Preparation of a novolak cyanate 100 g of novolak (Durite® SD-333 A, manufacturer: Borden Chem. Co.) were dissolved in 564 g of butyl acetate. The solution was cooled to about −15° C., then 67 g of gaseous cyanogen chloride were introduced. Then, over the course of about 30 min, 104 g of triethylamine were added dropwise with stirring, the temperature being kept below −10° C. After a further 30 min at this temperature, the cooling was removed and the reaction mixture was filtered. A sample obtained by evaporating the filtrate contained 190 ppm of triethylamine and 74 ppm of chloride. The filtrate was passed successively over a column comprising 100 ml of Lewatit® S100 (cation exchanger, H$^+$ form) and a column comprising 100 ml of Lewatit® MP62 (anion exchanger, OH$^-$ form). The ion exchangers had previously been regenerated with 5% hydrochloric acid and 4% sodium hydroxide solution, respectively, rinsed with water until neutral, dewatered with acetone and finally rinsed with butyl acetate. The solvent was then firstly distilled off at a bath temperature of 70° C. in a water-pump vacuum. The resulting material had a gelling time of from 30 to 47 min at 200° C., a triethylamine content of 31 ppm and a chloride content of 4 ppm. Finally, volatile impurities (including solvent residues, free triethylamine, diethylcyanamide) were removed in a falling-film evaporator at 1 mbar and 130° C.

The resulting product had a gelling time of 50 min at 200° C. and a viscosity of 284 mP.s.

EXAMPLE 2

Preparation of 2,2-bis(4-cyanatophenyl)propane (bisphenol A dicyanate)

150 g of bisphenol A were dissolved in 480 g of acetone, The solution was cooled to from −25 to −20° C., then, at this temperature, 88 g of cyanogen chloride were introduced over the course of 15 min. Then, over the course of about 1 h, 136 g of triethylamine were added dropwise, the temperature being kept at about −15° C. and triethylammonium chloride precipitating out. After a further 30 min, cooling was stopped, the reaction mixture was filtered and the filter cake was washed with acetone. The combined filtrates were halved (each about 600 ml). One half was, in accordance with the invention, firstly stirred with 50 g of Lewatit® S100 (cation exchanger, H$^+$ form) and then (after filtering off the ion exchanger) with 50 g of Amberlite® IRA-68 (strongly basic anion exchanger, OH$^-$ form) and then filtered again. The resulting solution was concentrated by evaporation under reduced pressure to about 200 ml, and then 250 ml of water were added.

The remaining acetone was distilled off, and the product which precipitated out was filtered off and dried under reduced pressure at 50° C. for 24 h.

The chloride content of the resulting product was 2 ppm.

EXAMPLE 3

Preparation of a novolak cyanate 103 g (1 equivalent) of novolak (Durite® SD-1711, manufacturer: Bordon Chem. Co.; corresponds to formula I where A=CH$_2$, R$^1$ to R$^{11}$=H, n=1 to 10) were dissolved in 422 g of acetone in a double-walled reaction vessel at room temperature. The solution was cooled to about −15° C., then, over the course of 15–20 min, 66.4 g (1.06 mol) of gaseous cyanogen chloride were introduced, the temperature being kept at −18 to −14° C. Then, over the course of about 30 min, 103.4 g (1.022 mol) of triethylamine were added dropwise with stirring, the temperature being kept at from −19 to −12° C. The cooling was then reduced such that the reaction mixture warmed to −5° C. over the course of about 30 min. After a further 30 min at this temperature, the mixture was again cooled to −15° C. The resulting suspension was filtered through a glass frit at this temperature. The filter cake was washed with 3×50 ml of acetone at −15° C. and dried. (The resulting triethylammonium chloride was used to recover the triethylamine.) The filtrate was combined with the wash solutions and, at room temperature and a through-put flow rate of 200 ml/min, was filtered successively through 50 ml each of a strongly acidic cation exchanger (Lewatit® S 100) and a weakly basic anion exchanger (Lewatit® MP 62). Both exchanger columns were then washed with 2×50 ml of acetone. As a result of the ion exchanger treatment, the chloride content of the solution was reduced from 297 ppm to 58 ppm and the triethylamine content from 572 ppm to 6 ppm. The solvent was distilled off on a rotary evaporator, the bath temperature being increased from 45° C. to 60° C. and the pressure being reduced from 500 mbar to 50 mbar. The residue was mixed thoroughly with 11.4 g of cyclohexanone (as entrainer) and then, for removal of the diethylcyanamide and the cyclohexanone, passed through a falling-film evaporator at a film temperature of 130° C. and about 2 mbar. The receiver was heated to 80° C. in order to keep the product liquid. The viscous product was then poured onto a chilled steel plate and the resulting solidified mass was comminuted.

Yield: 83.3 g
Gelling time: 10–20 min at 200° C.
Diethylcyanamide: ≦0.1%

Comparative Example

Preparation of 2,2-bis(4-cyanatophenyl)propane 250 ml of water were directly added to the second half of the filtrate from Example 2, and all of the acetone was distilled off. The product which precipitated out was filtered off and dried at 50° C. under reduced pressure for 24 h.

The chloride content of the resulting product was 14 ppm.

What is claimed is:

1. A process for the preparation of aryl cyanates comprising reacting a polyhydric phenol with a cyanogen halide in the presence of a tertiary amine and a nonaqueous solvent at low temperature, and subsequent removal of the formed tertiary ammonium halide from the reaction mixture, with some or all of the ammonium halide being removed by treatment of the nonaqueous reaction mixture with cation and anion exchangers.

2. The process according to claim 1, wherein the solvent is one in which the formed ammonium halide is not readily soluble, and most of the ammonium halide is separated off by filtration or centrifugation prior to ion exchange treatment.

3. The process according to claim 2, wherein the optionally filtered or centrifuged reaction mixture is treated first with a strongly acidic cation exchanger and then with a weakly basic anion exchanger.

4. The process according to claim 3, wherein the solvent is selected from the group consisting of dichloromethane, di-$C_{1-4}$-alkyl ketones, $C_{1-4}$-alkyl $C_{2-4}$-alkanoates, tetrahydrofuran and acetonitrile.

5. The process according to claim 4, wherein the solvent is dichloromethane, acetone or butyl acetate.

6. The process according to claim 5, wherein an aryl cyanate of the formula:

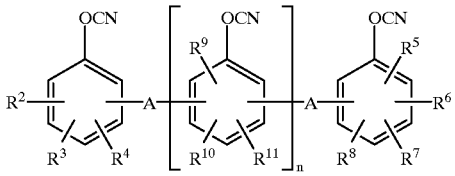

in which n is an integer from 0 to 20, the symbols A are in each case a direct chemical bond or a divalent group, and $R^1$ to $R^{11}$ independently of one another are hydrogen, halogen, $C_{1-4}$-alkoxy, $C_{1-4}$-alkylthio, $C_{1-4}$-alkoxycarbonyl or $C_{1-4}$-alkyl which is optionally completely or partially substituted by fluorine, is prepared.

7. The process according to claim 1, wherein the optionally filtered or centrifuged reaction mixture is treated first with a strongly acidic cation exchanger and then with a weakly basic anion exchanger.

8. The process according to claim 1, wherein the solvent is selected from the group consisting of dichloromethane, di-$C_{1-4}$-alkyl ketones, $C_{1-4}$-alkyl $C_{2-4}$-alkanoates, tetrahydrofuran and acetonitrile.

9. The process according to claim 8, wherein the solvent is dichloromethane, acetone or butyl acetate.

10. The process according to claim 1, wherein an aryl cyanate of the formula:

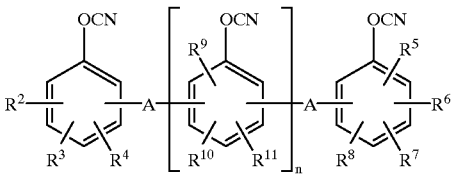

in which n is an integer from 0 to 20, the symbols A are in each case a direct chemical bond or a divalent group, and $R^1$ to $R^{11}$ independently of one another are hydrogen, halogen, $C_{1-4}$-alkoxy, $C_{1-4}$-alkylthio, $C_{1-4}$-alkoxycarbonyl or $C_{1-4}$-alkyl which is optionally completely or partially substituted by fluorine, is prepared.

* * * * *